US006071736A

United States Patent [19]
Perron et al.

[11] Patent Number: 6,071,736
[45] Date of Patent: *Jun. 6, 2000

[54] PROCESS AND CULTURE MEDIUM FOR THE PRODUCTION OF CELLS INFECTED BY A MULTIPLE SCLEROSIS-ASSOCIATED VIRUS

[75] Inventors: Herve Perron, Grenoble; Jean-Marie Seigneurin, Bernin, both of France

[73] Assignee: Bio Merieux, Marcy l'Etoile, France

[ * ] Notice: This patent is subject to a terminal disclaimer.

[21] Appl. No.: 08/754,010

[22] Filed: Nov. 20, 1996

Related U.S. Application Data

[63] Continuation of application No. 08/157,061, Feb. 2, 1994, Pat. No. 5,650,318.

[30] Foreign Application Priority Data

Nov. 3, 1992 [FR] France ................................... 92 13443
Apr. 3, 1993 [FR] France ................................... 92 04322

[51] Int. Cl.$^7$ .............................. C12N 7/00; C12N 5/00; A61K 37/12; A01N 63/00
[52] U.S. Cl. ................................. 435/235.1; 435/240.21; 435/239; 424/204.1; 424/184.1; 424/93.2
[58] Field of Search ........................... 435/240.21, 235.1, 435/239; 424/184.1, 93.2, 204.1

[56] References Cited

U.S. PATENT DOCUMENTS

| | | |
|---|---|---|
| 4,311,686 | 1/1982 | Angers et al. . |
| 4,346,074 | 8/1982 | Gilmour et al. . |
| 4,388,298 | 6/1983 | Nazerian et al. . |
| 4,396,600 | 8/1983 | Messineo et al. . |
| 4,520,113 | 5/1985 | Gallo et al. . |
| 4,647,773 | 3/1987 | Gallo et al. . |
| 4,708,818 | 11/1987 | Montagnier et al. . |
| 4,900,553 | 2/1990 | Silver et al. . |
| 5,158,976 | 10/1992 | Rosenburg et al. . |
| 5,219,837 | 6/1993 | Cohen et al. . |
| 5,225,352 | 7/1993 | Zanetta et al. . |
| 5,585,262 | 12/1996 | Perron et al. . |
| 5,650,318 | 7/1997 | Perron . |

FOREIGN PATENT DOCUMENTS

| | | |
|---|---|---|
| 0 222 310 | 5/1987 | European Pat. Off. . |
| 0 326 395 | 8/1989 | European Pat. Off. . |
| 93/07259 | 4/1993 | WIPO . |
| 93/20188 | 10/1993 | WIPO . |
| WO 93/23550 | 11/1993 | WIPO . |
| WO 94/28138 | 12/1994 | WIPO . |

OTHER PUBLICATIONS

Acha–Orbea et al., "Mls—A Retrovirus Exploits the Immune System", *Immunology Today*, vol. 12, No. 10, 1991, pp. 356–361.

Asai et al., "J. of Neurochem", vol. 59, No. 1, pp. 307–317, 1992.

*ATTC Catalogue of Cell Lines and Hybridomas*, Sixth Edition, 1988, pp. 165 and 344–355.

R. Baccala et al., "Genomically Imposed and Somatically Modified Human Thymocyte vb Gene Repertoires", *Proc. Natl. Acad. Sci.*, vol. 88, p. 2908, 1991.

Barna et al., "Human Astrocytes Proliferate in Response to Tumor Necrosis Factor Alpha", *J. Neuroimmunol.*, 30 (1990), pp. 239–243.

Beck et al., "Increased Production of Interferon Gamma and Tumor Necrosis Factor Precedes Clinical Manifestation in Multiple Sclerosis: Do Cytokines Trigger Off Exacerbations?", *Acta Neurol. Scand.*, 1988: 78, pp. 318–323.

Bergamini et al., "Multiple Sclerosis. I. The Immune Pathogenetic Hypothesis", *Riv. Neurol.*, vol. 59, No. 5, Oct. 1989, pp. 176–190.

T. Bergström et al., "Isolation of Herpes Virus Type 1 During First Attack of Multiple Sclerosis.", *Annales Neurology*, vol. 26, pp. 283–285, (1989).

Bernton et al., "No Direct Neuronotoxicity by HIV–1 Virions or Culture Fluids from HIV–1 Infected T Cells or Monocytes", *Aids Research and Human Retroviruses*, vol. 8, No. 4, 1992, pp. 495–503.

Birnbaum et al., "Spinal Fluid Lymphocytes from a Sub-Group of Multiple Sclerosis Patients Respond to Mycobacterial Antigens", *Ann. Neurol.*, vol. 34, No. 1, Jul. 1993, pp. 18–24.

Bjare, "Serum–Free Cell Culture", *Pharmac. Ther.*, vol. 53, 1992, pp. 355–374.

C. Bosgiraud et al., "Ultrastructural Study on Visna Virus in Sheep Plexus Choroid Cells", Biological Abstracts, vol. 83, No. 7, 1987.

D. Ross Boswell et al., "Sequence comparison and alignment: the measurement and interpretation of sequence similarity", *Computational Molecular Biology, Sources and Methods for Sequence Analysis*, pp. 161–178.

Boyle et al., "Cellular Immune Response in Multiple Sclerosis Plagues", *American Journal of Pathology*, vol. 137, No. 3, Sep. 1990, pp. 575–584.

Bradford, A Rapid and Sensitive Method for the Quantitation of Microgram Quantities of Protein Utilizing the Principle of Protein–Dye Binding, *Anal. Biochem.*, 72, 1976, pp. 248–254.

Brocke et al., "Induction of Relapsing Paralysis in Experimental Autoimmune Encephalomyelitis by Bacterial Superantigen", *Nature*, vol. 365, Oct. 14, 1993, pp. 642–644.

(List continued on next page.)

*Primary Examiner*—Nita Minnifield
*Attorney, Agent, or Firm*—Oliff & Berridge, PLC

[57] ABSTRACT

In a process for the in vitro production of a culture or cell line infected by a viral strain associated with multiple sclerosis (MS), a body sample is taken from an individual suffering from MS. The sample is cultivated in a culture medium that promotes the growth of infected cells to obtain a culture of primary infected cells. A sample of the culture of primary cells or a subculture of the latter is cultivated in series, by successive passages in the culture medium to obtain the culture or cell line infected by a virus associated with MS. The culture medium also contains a beta-interferon antibody or an antibody that is directed against an antigenically close molecule, the antibody playing an inhibiting role in viral expression and allowing long-lasting expression and propagation of the viral strain in the culture or cell line.

13 Claims, 5 Drawing Sheets

OTHER PUBLICATIONS

Calder, et al., "MS: A Localized Immune Disease of the Central Nervous System", *Immunology Today*, vol. 10, No. 3, 1989, pp. 99–103.

Carp et al., "Viral Etiology of Multiple Sclerosis", *Prog. Med. Virol.*, vol. 24, pp. 158–177, 1978.

Charcot, "Histologie de la sclerose en plaques [Histology of Multiple Sclerosis]", Gaz. Hop. (Paris), 1868; 41, 554–66.

Chomczynski et al., "Single–Step Method of RNA Isolation by Acid Guanidinium Thiocyanate–Phenol–Chloroform Extraction", *Anal. Biochem.*, 1987, vol. 162, pp. 156–159.

Cole et al., "The Mycoplasma Arthritidis T–Cell Mitogen, MAM: A Model Superantigen", *Immunology Today*, vol. 12, No. 8, 1991, pp. 271–276.

Cook et al., "Multiple Sclerosis and Distemper in Iceland 1966–1978", *Acta Neurol. Scandinav.* 61, 1980, pp. 244–251.

Dalgleish et al., "Do Human T–Lymphotrophic Viruses (HTLVs) and Other Enveloped Viruses Induce Autoimmunity in Multiple Sclerosis?", *Neuropath. App. Neurobiol.*, 1987, 13, pp. 241–250.

A. N. Davison et al., "Biosynthesis of Myelin and Neurotoxic Factors in the Serum of Multiple Sclerosis Patients", *Advances in Experimental Medicine and Biology*, vol. 100, pp. 19–25, 1978.

De Keyser, "Autoimmunity in Multiple Sclerosis", *Neurology*, 38, Mar. 1988, pp. 371–374.

S. Dhib–Jalbut et al., "Measles Virus Polypeptide–Specific Antibody Profile in Multiple Sclerosis", *Neurology*, vol. 40, pp. 430–435, (1990).

Dunn et al., "A Novel Method to Map Transcripts: Evidence for Homology Between an Adenovirus mRNA and Discrete Multiple Regions of the Viral Genome", *Cell*, vol. 12, Sep. 1977, pp. 23–36.

Ebers et al., "The Geography of MS Reflects Genetic Susceptibility", *Neurology*, 36, Apr. 1986, Suppl. 1, p. 108.

Elian et al., "Multiple Sclerosis Among United Kingdom–Born Children of Immigrants from the Indian Subcontinent, Africa and the West Indies", *J Neurol Neurosurg Psychiat*, 1990; 53, pp. 906–911.

Escourolle et al., "Principales Donnees Morphologiques Approches Physiopathologiques et Etiologiques de la Sclerose en Plaques [Principal Morphological Data, Physiopathological and Etiological Approaches to Multiple Sclerosis]", *La Reveue du Praticien*, Paris, 1980; 30, pp. 2047–2053.

Frohman et al., "Rapid Production of Full–Length cDNAs from Rare Transcripts: Amplification Using a Single Gene–Specific Oligonucleotide Primer", *Proc. Natl. Acad. Sci. USA*, 1988, vol. 85, pp. 8998–9002.

Medline Abstract of FU et al., "Rabies virus nucleoprotein expressed in and purified from insect cells is efficacious as a vaccine," Proc Natl Acad Sci USA 88: 2001–05 (1991).

Galiana et al., "Establishment of Permanent Astroglial Cell Lines, Able to Differentiate in Vitro, From Transgenic Mice Carrying the Polyoma Virus Large T Gene: An Alternative Approach to Brain Cell Immortalization", *Journal of Neuroscience Research*, 1990; 26: pp. 269–277.

M. B. Gardner et al., "Congenital Transmission of Murine Leukaemia Virus from Wild Mice Prone to Development of Lymphoma and Paralysis", *J. Natl. Cancer Inst.*, vol. 62, pp. 63–69, (1979).

M. B. Gardner, Genetic resistance to a Retroviral Neurologic Disease in Wild Mice, in "Retrovirus Infections of the Nervous System", Oldstone M.B.A. and Koprowsky H. Eds. *Current Topice in Microbiology and Immunology*, No. 160, pp. 3–10, (Springer–Verlag, Berlin, 1990).

Gay, "Is Multiple Sclerosis Caused by an Oral Spirochaete", *The Lancet*, Jul. 12, 1986, pp. 75–77.

A. Gessain et al., Antibodies to Human T–Lymphotrophic Virus type–I in Patients with Tropical Spastic Paraparesis, *Lancet*, vol. 2, pp. 407–410, (1985).

Giulian et al., "The Envelope Glycoprotein of Human Immunodeficiency Virus Type 1 Stimulates Release of Neurotoxins from Monocytes", *Proc. Natl. Acad. Sci. USA*, vol. 90, 1993, pp. 2769–2773.

D. Giulian et al., "Secretion of Neurotoxins by Mononuclear Phagocytes Infected with HIV–1", *Science*, vol. 250, Dec. 14, 1990, pp. 1593–1596.

Gonzalez–Scarano et al., "Multiple Sclerosis Disease Activity Correlates with Gadolinium–Enhanced Magnetic Resonance Imaging", *Annals of Neurology*, vol. 21, No. 3, Mar. 1987, pp. 300–306.

F. Gonzalez–Scarano et al., "Sequence Similarities Between Human Immunodeficiency Virus gp41 and Paramyxovirus Fusion Proteins.", *AIDS Res. Hum. Retrov.*, vol. 3, pp. 245–252, (1987).

S. Haahr et al., "A Putative New Retrovirus Associated with Multiple Sclerosis and the Possible Involvement of Epstein–arr Virus in this Disease", *NY Acad. Science*, vol. 724, pp. 148–156, 1994.

S. Haahr et al., "Is Multiple Sclerosis Caused by a Dual Infection with Retrovirus and Epstein–Barr Virus?", *Neuroepidemiology*, vol. 11, pp. 299–303, (1992).

Haegert et al. HLA–DRβ, –DQα, and –DQβ Restriction Fragment Length Polymorphisms in Mutiple Sclerosis, *J. Neurosci. Res.*, 1989; 23, pp. 46–54.

Hauw et al., "Aspects Anatomo–Pathologiques de la Sclerose en Plaques [Anatomopathological Aspects of Multiple Sclerosis]", *La Sclerose en Plaques [Multiple Sclerosis]*, 9–47 (Rascol et al. eds., 1980).

Hirayama et al., "Serum–Mediated Oligodendrocyte Cytotoxicity in Multiple Sclerosis Patients and Controls", *Neurology* 1986, vol. 36, pp. 276–278.

Hoffman et al., "Handbook of Clinical Neurology, 12; Virtual Diseases", R.R. McKendall, ed., Elsevier Science Publishing, Amsterdam, 1989, pp. 453–466.

Huang, "Defective Interfering Viruses", *Fundamental Virology*, Fields et al., eds., 1986, pp. 101–117.

Huck et al., "J. of Neurosei", vol. 4, No. 10, pp. 2650–2657, 1984.

A. W. Hugin et al., "A Virus–Encoded Superantigen in a Retrovirus–Induced Immunodeficiency Syndrome of Mice", *Science*, vol. 252, pp. 424–427, (1991).

James, "Multiple Sclerosis or Blood–Brain Barrier Disease", *The Lancet*, Jan. 7, 1989, p. 46.

Medline abstract of Jarrett et al., "Studies on vaccination against papillomaviruses: a comparison of purified virus, tumour extract and transformed cells in prophylactic vaccination," Vet Rec 126: 449–52 (1990).

Jervis et al., "Experimental Allergic Encephalomyelitis", *J. Neuropathol. Exp. Neurol.*, 1948; 7, pp. 309–320.

Johnson, "Viral Aspects of Multiple Sclerosis", *Handbook of Clinical Neurology*, vol. 3(47): Demyelinating Diseases, 1985, pp. 319–336.

R.T. Johnson, "Nononcogenic Retrovirus Infections as Models for Chronic and relapsing Human Diseases: Introduction", *Reviews of Infectious Diseases*, vol. 7, No. 1, Jan.–Feb. 1985, pp. 66–67.

Juntunen et al. "Multiple Sclerosis and Occupational Exposure to Chemicals: A Co–Twin Study of a Nationwide Series of Twins", *Br. J. Int. Med.*, 1989; 46: pp. 417–419.

Karpas et al., "Lack of evidence for involvement of known human retroviruses in multiple sclerosis", *Nature*, vol. 322, Jul. 10, 1986, pp. 177–178.

Kent et al., "Cerecral Blood Flow, Cerebral Metabolism and Blood Flow, Cerebral Metabolism and Blood–Brain Barrier," *Handbook of Clinical Neurology*, vol. 56(12), 1989, pp. 79–91.

G. La Mantia et al., "Identification of New Human Repetitive Sequences: Characterization of the Corresponding cDNAs and their Expression in Embryonal Carcinoma Cells", *Nucleic Acids Research*, vol. 17, No. 15, 5913–5922, (1989).

G. La Mantia et al., "Identification and Characterization of Novel Human Endogenous Retroviral Sequences Prefentially Expressed in Undifferentiated Embryonal Carcinoma Cells", *Nucleic Acids Res.*, 1991, vol. 19, No. 7, pp. 1513–1520.

Medline abstract of LEAO, "Tuberculosis: new strategies for the development of diagnostic tests and vaccines," Braz J Med Biol Res 26: 827–33 (1993).

Levi et al., Human Immunodeficiency Coat Protein gp120 Inhibits the β–adrenergic Regulation of Astroglial and Microglial Functions, *Proc. Natl. Acad. Sci. USA*, vol. 90, Feb. 1993, pp. 1541–1545.

Levine et al., "Conversion of Lytic to Persistent Alphavirus Infection by the bcl–2 Cellular Oncogene", *Nature*, vol. 361, Feb. 25, 1993, pp. 739–742.

Y.S. Lie et al., Journal of Virology, vol. 68, No. 12, Dec. 1994, pp. 7840–7849, "Chinese hamster ovary cells contain transcriptionally active full length type C provirises".

Linial et al. , "Retrioviral RNA Packaging: Sequence Requirements and Implications", in *Current Topics in Microbiology and Immunobiology. Retroviruses, Strategies of Replication*, Swanstrom et al., eds., vol. 157, 1990, pp. 125–152.

Lo et al, "Newly Discovered Mycoplasma Isolated from Patients Infected with HIV", *The Lancet*, vol. 338, Dec. 7, 1991, pp. 1415–1418.

Lori et al., "Viral DNA Carried by Human Immunodeficiency Virus Type 1 Virions", *J. Virol.*, vol. 66, No. 8, Aug. 1992, pp. 5067–5074.

F. Mallet et al., "Continuous RT–PCR and taq DNA Polymerase: Characterization and Comparison to Uncoupled Procedures", *Biotechniques*, vol. 18, pp. 678–687, 1985.

Mallet et al., "Enzyme–Linked Oligosorbent Assay for Detection of Polymerase Chain Reaction–Amplified Human Immunodeficiency Virus Type I ", *J. Clin. Microbiol.*, Jun. 1993, vol. 31, No. 6, pp. 1444–1449.

Marie, "Sclerose en Plaques et Maladies Infectieuses [Multiple Sclerosis and Infectious Diseases]", *Le Progres Medical*, 1884; 12, pp. 287–289.

P. Marrack et al., "A Maternally Inherited Superantigen Encoded by a Mammary Tumor Virus", *Nature*, vol. 349, pp. 524–526, (1991).

McDonald, "The Mystery of the Origin of Multpile Sclerosis", *J. Neurol. Neurosurg. Psych.*, 1986; 49, pp. 113–123.

J. Meregaert et al., "Necleotide Sequence of a Radiation Leukemia Virus Genome", *Virology* vol. 158, No. 1, pp. 88–102, (1987).

Meyerhans et al., "Temporal Fluctuations in HIV Quasispecies in Vivo Are Not Reflected by Sequential HIV Isolation", *Cell*, vol. 58, Sep. 8, 1989, pp. 901–910.

Mosmann, "Rapid Colorimetric Assay for Cellular Growth and Survival: Application to Proliferation and Cytotoxicity Assays", *Journal of Immunological Methods*, 65, 1983, pp. 55–63.

Newell et al., "Ligation of Major Histocompatibility Complex Class II Molecules Mediates Apoptotic Cell Death in Resting B Lymphocytes", *Proc. Natl. Acad. Sci. USA*, vol. 90, Nov. 1993, pp. 10459–10463.

Nielsen et al., "Sequence–Selective recognition of DNA by Strand Displacement with a Thymine–Substituted Polyamide", *Science*, vol. 254, pp. 1497–1500, 1991.

Norby, "Viral Antibodies in Multiple Sclerosis", *Prog. Med. Virol.*, vol. 24 1978, pp. 1–39.

Medline abstract of Orlandi et al., "Characterization of the 175–kilodalton erythrocyte binding antigen of Plasmodium falciparum," Mol Biochem Parasitol 40: 285–94 (1990).

Ostrove et al., "Activation of the Human Innumodeficiency Virus by Herpes Simplex Virus Type 1", J Virol 61(12), Dec. 1987, pp. 3726–3732.

J.L. Pablos et al., "A novel retroviral POL sequence is present in patients with rheumatoid arthritis", & American College of Rheumatology 57th Annual Scientific Meeting, Nov. 7–11, 1993 San Antonio, Texas, USA, *Arthritis and Rheumatism*, vol. 36, No. 9 supl. 1993, p. S55, Abstract No. 102.

Medline abstract of PEI et al., "Identification, purification, and characterization of major antigenic proteins of Campylobacter jejuni," J Biol Chem 266: 16363–69 (1991).

H. Perron et al., "Leptomeningeal cell line from multiple sclerosis with reverse transcriptase activity and viral particles", *Res. Virol.*, Nov. 1989, vol. 140(6), pp. 551–561.

H. Perron et al., "Retrovirus Isolation from Patients with Multiple Sclerosis: Epiphenomenon or Causative Factor?", *AIDS Research and Human Retroviruses*, vol. 8, No. 5, May 1992, p. 922.

H. Perron et al., "In Vitro Transmission and Antigenicity of a Retrovirus Isolated from a Multiple Sclerosis Patient", *Res. Virol.*, vol. 143, No. 5, 1992, pp. 337–350.

Perron et al., "Retroviral Reactivation by Herpesviruses in MS: Serological Arguments", Current Concepts in Multiple Sclerosis 1991, pp. 331–332.

A. Plaza et al., Theofilopoulos, A.N. New Human vβ 12DD Genes and Polymorphic Variants. J. Imm; vol. 147, No. 12, pp. 4360–4365, 1991.

Poirier et al., "La Barriere Hemato–Encephalique. Donnees Morphologiques [The Blood–Brain Barrier. Morphological Data]", *La Revue de Medecine Interne*, vol. IV, No. 2, Jun. 1983, pp. 131–144.

J. L. Portis, Wild Mouse Retrovirus: Pathogenesis in "Retrovirus Infections of the Nervous System". Oldstone M.B.A. and Koprowsky H. Eds. Current topics in microbiology and immunology, No. 160, pp. 11–27, (Springer–Verlag, Berlin, 1990).

C. M. Poser et al., "New Diagonostic Criteria for Multiple Sclerosis: Guidelines for Research Protocols, in "The diagnosis of Multiple Sclerosis", *Thieme Stratton Inc.*, pp. 225–229, 1984.

D.N., Posnet, "Do Superantigens Play a Role in Autoimmunity?", *Semin. Immunol.*, vol. 5, pp. 65–72, 1993.

Prineas, "The Neuropathology of Multiple Sclerosis", *Handbook of Clinical Neurology*, vol. 3 (47), 1985, pp. 213–257.

Prineas et al., "Mutiple Sclerosis: Remyelination of Nascent Lesions", *Annals of Neurology*, vol. 33, No. 2, Feb. 1993, pp. 137–151.

Prineas, "Pathology of the Early Lesion in Multiple Sclerosis", *Human Pathology*, vol. 6, No. 5, Sep. 1975, pp. 531–554.

Prineas et al., "Macrophages, Lymphocytes and Plasma Cells in the Perivascular Compartment in Chronic Multiple Sclerosis", *Laboratory Investigation*, vol. 38, No. 4, 1978, pp. 409–421.

Ransohoff et al., "Heat–Shock Proteins and Autoimmunity: Implications for Multiple Sclerosis", *Annals of Neurology*, vol. 34, No. 1, Jul. 1993, pp. 5–7.

Rapoport, *Blood–Brain Barrier in Physiology and Medicine*, 129 (1976).

S. S. Rhee et al., "A single Amino Acid Substitution Within the Matrix Protein of the D–Type Retrovirus Converts Its Morphogenesis to that of a C–Type Retrovirus", Cell 63, pp. 77–86, (1990).

Riise et al., "Clustering of Residence of Multiple Sclerosis Patients at Age 13 to 20 Years in Hordaland, Norway", *Am J Epidemiol* 1991, vol. 133, No. 9, pp. 932–939.

Robbins et al., "Production of Cytotoxic Factor for Oligodendrocytes by Stimulated Astrocytes", *The Journal of Immunology*, vol. 139, No. 8, Oct. 15, 1987, pp. 2593–2597.

Rosati et al., "Incidence of Multiple Sclerosis in the Town of Sassari, Sardinia, 1965 to 1985: Evidence for Increasing Occurrence of the Disease", *Neurology* 38 (Mar. 1988), pp. 384–388.

Rudge, "Dose a Retrovirally Encoded Superantigen Cause Multiple Sclerosis?", *J. Neurology Neurosurgery & Psychiatry* 1991, vol. 54, pp. 853–855.

Medline abstract of Rumschlag et al., "Immunologic characterization of a 35–kilodalton recombinant antigen of *Mycobacterium tuberculosis*", J Clin Microbiol 28: 591–95 (1990).

Medline abstract of Sakulramrung et al., "Antigenic and immunogenic characteristics of subcellular fractions and whole cells of a rough E. coli 0111 (J5) mutant," Immunobiology 169: 372–88 (1985).

Selmaj, et al., "Tumor Necrosis Factor Mediates Myelin and Oligodendrocyte Damage In Vitro", *Annals of Neurology*, vol. 23, No. 4, Apr. 1988, pp. 339–346.

Shih et al., "Detection of Multiple, Novel Reverse Transcriptase Coding Sequences in Human Nucleic Acids: Relation to Primate Retroviruses", *J. Virol.*, Jan. 1989, vol. 63, No. 1, pp. 64–75.

Silberberg et al., "Tissue Culture Demyelination by Normal Human Serum", *Annals of Neurology*, vol. 15, No. 6, Jun. 1994, pp. 575–580.

M. Sommerlund et al., "Retrovirus–like particles in an Epstein–Barr virus–producing cell line derived from a patient with chronic progressive myelopathy", *Acta Neurol Scand*, 1993: 87: pp. 71–76.

P. Sonigo et al., "Nucleotide Sequence of Mason–Pfizer Monkey Virus: An immunosuppressive D–Type Retrovirus", Cell 45, pp. 375–385, (1986).

Southern, "Detection of Specific Sequences Among DNA Fragments Separated by Gel Electrophoresis", *J. Mol. Biol.*, 1975, vol. 98, pp. 503–517.

Suzumura et al., "Serum Cytotoxicity to Oligodendrocytes in Multiple Sclerosis and Controls: Assessment by $^{51}$Cr Release Assay", *J. Neuroimmunol.*, 11 (1986), pp.137–147.

Traugott, "Multiple Sclerosis: Relevance of Class I and Class II MHC–Expressing Cells to Lesion Development", *Journal of Neuroimmunology*, 16, 1987, pp. 283–302.

Waksman, "Mechanisms in Multiple Sclerosis", *Nature*, vol. 318, Nov. 14, 1985, pp. 104–105.

Williams et al., "Molecular Regulation of Apoptosis: Genetic Controls on Cell Death", *Cell*, vol. 74, Sep. 10, 1993, pp. 777–779.

Wienfield et al., "Stress Proteins, Autoimmunity, and Autoimmune Disease", *Current Topics in Microbiology and Immunology*, vol. 167, Springer–Verlag, Berlin, 1991, pp. 161–189.

D. L. Wilkinson et al., "Evidence for a functional subclass of the RTLV–H family of human endogenous retrovirus–like sequences", *J. Virol.*, vol. 67, pp. 2981–2989, (1993).

Wollinsky et al., "Liquorpherese bei 10 Patienten mit Multipler Sklerose [Fluid Phoresis in 10 Patients With Multiple Sclerosis]", *Verhandlungen der Deutschen Gesellschaft fir Neurologie*, vol. 7, 1992, pp. 444–445.

Woodland, et al., "An Endogenous Retrovirus Mediating Deletion of αβ T cells?", *Nature*, vol. 349, Feb. 7, 1991, pp. 529–530.

Charcot, "Histologie de la sclerose en plaques [Histology of Multiple Sclerosis]", Gaz. Hop. (Paris), 1868; 41, 554–566.

Escourolle et al., "Principales Donnees Morphologiques Approches Physiopathologiques et Etiologiques de la Sclerose en Plaques [Principal Morphological Data, Physiopathological and Etioogical Approaches to Multiple Sclerosis]", *La Reveue de Praticien*, Paris, 1980; 30, pp. 2047–2053.

Hauw et al., "Aspects Anatomo–Pathologiques de la Scleroseen Plaques [Anatomopathological Aspects of Multiple Sclerosis]", *La Sclerose en Plaques [Multiple Sclerosis]*, 9–47 (Rascol et al. eds., 1980).

Marie, "sclerose en Plaques et Maladies Infectieuses [Multiple Sclerosis and Infectious Diseases]", *Le Progres Medical*, 1884; 12, pp. 287–289.

Poirier et al., "La Barriere Hemato–Encephalique. Donnees Morphologiques [The Blood–Brain Barrier. Morphological Data]", *La Revue de Medecine Interne*, vol. IV, No. 2, Jun. 1983, pp. 131–144.

Wollinsky et al., "Liquorpherese bei 10 Patienten mit Multipler Sklerose [Fluid Pheresis in 10 Patients With Multiple Sclerosis]", *Verhandlungen der Deutschen Gesellschaft fur Neurologie*, vol. 7, 1992, pp. 444–445.

H. Perron et al., "Leptomeningeal Cell Line from Multiple Sclerosis with Reverse Transcriptase Activity and Viral Particles", Biological Abstracts, vol. 89, No. 9, May 1, 1990.

H. Perron et al., "Isolation of Retrovirus from Patients with Multiple Sclerosis", *The Lancet*, vol. 337, No. 8745, Apr. 6, 1991, pp. 862–863.

H. Perron et al., "Antibody to Reverse Transcriptase of Human Retrovirus in Multiple Sclerosis", Biological Abstracts, vol. 93, No. 6, Mar. 15, 1992.

J. D. Mosca et al., "Activation of Human Immunodeficiency Virus by Herpesvirus Infection: Identification of a Region Within the Long Terminal Repeat that responds to a Trans––Acting Factor Encoded By Herpes Simplex Virus 1", *Proceedings of the National Academy of Sciences of USA*, vol. 84, No. 1, Nov. 1987, pp. 7408–7412.

H. Perron et al., "Herpes Simplex Virus ICPO and ICP4 Immediate Early Proteins Strongly Enhance Expression of a Retrovirus Harboured by a Leptomeningeal Cell Line from a Patient with Multiple Sclerosis", *The Journal of General Virology*, vol. 74, No. 1, Jan. 1993, pp. 65–72.

R. Lisak et al., "In Vitro Cell–Mediated Immunity of Cerebrospinal–Fluid Lymphocytes to Myelin Basic Protein In Primary Demyelinating Diseases", *The New England Journal of Medicine*, vol. 297, No. 16, Oct. 20, 1977, pp. 850–853.

C. R. Bangham et al., "PCR Analysis of DNA from Multiple Sclerosis Patients for the Presence of HTLV–I", *Science*, vol. 246, Nov. 10, 1989, pp. 821–824.

E.J. Field, "Immunological Treatment for Multiple Sclerosis", *The Lancet*, Jun. 3, 1989, p. 1972.

D. Johnson et al., "Quantitation of the Myelin–Associated Glycoprotein in Human Nervous Tissue from Controls and Multiple Sclerosis Patients", *Journal of Neurochemistry*, vol. 46, No. 4, 1986, pp. 1086–1093.

S. L. Hauser et al., "Analysis of Human T–lymphotropic Virus Sequences in Multiple Sclerosis Tissue", *Nature*, vol. 322, Jul. 10, 1986, pp. 176–178.

H. Lassmann et al., "Chronic Relapsing Experimental Allergic Encephalomyelitis Clinicopathological Comparison with Multiple Sclerosis", *Arch Neurol*, vol. 36, Aug. 1979, pp. 490–497.

A. T. Hasse, "Pathogenesis of Lentivirus Infections", *Nature*, vol. 322, Jul. 10, 1986, pp. 130–136.

N. Nathanson et al., "Experimental Visna in Icelandic Sheep: The Prototype Lentriviral Infection", *Reviews of Infectious Diseases*, vol. 7, No. 1, Jan.–Feb. 1985, pp. 75–82.

S. HAAHR et al., "Just Another Dubious Virus in Cells from a Patient with Multiple Sclerosis?", *The Lancet*, vol. 337, Apr. 6, 1991, pp. 863–864.

M. Ohta et al., "Sera from Patients with Multiple Sclerosis react with Human T Cell Lymphotropic Virus–I Gag Proteins But Not Env Proteins—Western Blotting Analysis", *The Journal Of Immunology*, vol. 137, No. 11, Dec. 1, 1986, pp. 3440–3443.

H. Koprowski et al., "Multiple Sclerosis and Human T–Cell Lymphotropic Retrovirusus", *Nature*, vol. 318, Nov. 14, 1985, pp. 154–160.

S.J., Greenberg et al., "Detection of Sequences Homologous to Human retroviral DNA in Multiple Sclerosis by Gene Amplification", *Proc. Natl. Acad. Sci. USA*, vol. 86, Apr. 1989, pp. 2878–2882.

E. P. Reddy et al., "Amplification and Molecular Cloning of HTLV–I Sequences from DNA of Multiple Sclerosis Patients", *Science*, vol. 243, Jan. 27, 1989, pp. 529–533.

K. G. Warren et al., "Diagnostic Value of Cerebrospinal Fluid Anti–Myelin Basic Protein in Patients with Multiple Sclerosis", *Annals of Neurology*, vol. 20, No. 1, Jul. 1986, pp. 20–25.

O. Narayan et al., "Lentiviral Diseases of Sheep and Goats: Chronic Pneumonia Leukoencephalomyelitis, and Arthritis", *Reviews of Infectiuos Diseases*, vol. 7, No. 1, Jan.–Feb. 1985, pp. 89–98.

A. Gessain et al., "Intrathecal Synthesis of Antibodies to Human T Lymphotropic Virus Type I and the Presence of IgG Oligoclonal Bands in the Cerebrospinal Fluid of Patients with Endemic Tropical Spastic Paraparesis", *The Journal of Infectious Diseases*, vol. 157, No. 6, Jun. 1988, pp. 1226–1234.

PROCESS AND CULTURE MEDIUM FOR THE PRODUCTION OF CELLS INFECTED BY A MULTIPLE SCLEROSIS-ASSOCIATED VIRUS

This is a Continuation of application Ser. No. 08/157,061 filed Feb. 2, 1994 now U.S. Pat. No. 5,650,318.

BACKGROUND OF THE INVENTION

The present invention relates to a medium for in vitro culture of cells infected by a virus present in individuals suffering from multiple sclerosis, a process for the production of infected cells using said medium and the infected cell lines thus obtained

DESCRIPTION OF THE PRIOR ART

Multiple sclerosis (MS) is a demyelinizing disease of the central nervous system (CNS) which has been suspected for several years of being associated with a virus, although the causal agent still has not been determined with certainty.

Several works have supported this hypothesis of a viral etiology of the disease, but none of the known viruses tested has proved to be the causal agent sought.

Consequently, the observation in patients suffering from multiple sclerosis of phenomena comparable to an autoimmunity reaction has led to an "essential" autoimmune etiological hypothesis (Lisak R. P., Zweiman B. New Engl. J. Med. 1977; 297, 850–853, and Lassmann H. and Wisniewski N. M. Arch. Neurol. 1979; 36, 490–497). However, this autoimmunity directed against certain components of the central nervous system has proven to be not very specific to MS and frequent in inflammations of the CNS, which may or may not be associated with an infection, as was demonstrated by Hirayama M. et al. (Neurology 1986; 36, 276–8) Kenneth G. Warren et al. (Annals of Neurology 1986; 20, 20–25), Suzumura A. et al. (Journal of Neuroimunology 1986; 11, 137–47) and Tourtelotte W. et al. (Journal of Neurochemistry 1986; 46, 1086–93). Furthermore, as noted by E. J. Field (The Lancet 1989; 1, 1272), none of the immunosuppressive therapeutic agents has allowed decisive results against MS to be obtained.

One hypothesis has been put forward, according to which a retrovirus is said to be the cause of the disease. The discovery by A. Gessain et al. (J. Infect. Disease 1968; 1226–1234) of neurological syndromes associated with the HTLV-1 virus, known originally as an agent of T-cell leukemias in adults, has led several authors, such as H. Koprowski et al. (Nature 1985; 318, 154), M. Ohta et al. (J. Immunol. 1986; 137, 3440), E. P. Reddy et al. (Science 1989; 243, 529), S. J. Greenberg et al. (Proc. Natl. Acad. Sci. USA 1989; 86, 2878), J. H. Richardson et al. (Science 1989; 246, 821), S. L. Hauser et al. (Nature 1986; 322, 176) and A. Karpas et al. (Nature 1986; 322, 177), to investigate an involvement of this human retrovirus in MS, but without success or with results which suggest cross-reactions.

There is furthermore an animal model which is very close to MS and is induced by a retrovirus: the MAEDI-VISNA virus of sheep. It is known that natural infection by this virus causes an ovine disease similar to MS, as reported by Johnson R. T. (Rev. Infect. Dis. 1985; 7, 66–67), Narayan O. and Cork L. C. (Rev. Infect. Dis. 1985; 7, 89–98) and Nathanson N. et al. (Rev. Infect. Dis. 1985; 7, 75–82). Experimental infection of sheep by intraventricular inoculation of neurovirulent strains of the Visna virus has allowed the responsibility of this virus in the origin of this demyelinizing infection of sheep to be established. As explained by Nathanson N. et al. (Rev. Infect. Dis. 1985; 7, 75–82), Hoffman P. M. and Panitch H. S. ("Handbook of Clinical Neurology, 12; Viral Diseases" R. R. McKendall, ed., Elsevier Science Publishing, Amsterdam, 1989, 453–466) and A. Haase (Nature 1986; 322, 130–136), it differs slightly from natural infection, but nevertheless remains close to MS. It is moreover interesting to note that in all the works carried out on this subject by the above-mentioned authors, the Visna virus is found in the cells of the plexus choroideus of the brain of infected sheep, which constitutes a site of dormancy and occasional replication of the Visna provirus; the location of these cells at the cephalorrachidian blood/fluid boundary certainly explains this phenomenon.

All these results argue in favor of the role of an unknown retrovirus in MS.

Works by H. Perron et al. (Res. Virol. 1989; 140, 551–561, and "Current concepts in multiple sclerosis" Wiethölter et al., editors Amsterdam, Elsevier, 1991, pages 111–116 and The Lancet 1991; 337, 862–663) have recently allowed isolation of a line of non-lymphoid cells from a lumbar puncture of the cephalorrachidian fluid of a patient suffering from MS and demonstration of the presence of a virus, having the characteristics of a retrovirus and showing in particular an reverse transcriptase activity, in the supernatant of the culture of the cells of this line. Examination of cells of this line by electron microscopy has allowed the demonstration of viral particles having a diameter of between about 110 and 140 nm, the size of the particles varying according to whether they are mature or immature particles. Furthermore, a serological study by the ELISA technique using a cell extract of infected cells of this line has shown, with 40 sera of patients among whom 20 are suffering from MS (certain MS) and 20 are presumed patients (probable MS), 60% of positive results. A comparative study with 40 sera of patients suffering from neurological diseases other than MS gave only 5% of positive results. This line, which the authors have called LM7, is clonal and non-immortal and immunocytochemical and ultrastructural study of the line has allowed characterization of its leptomeningeal origin.

However, this virus has proved to be very difficult to study because on the one hand it expresses itself very weakly in vitro in the primary cell line of leptomeningeal origin, and on the other hand this cell line degenerates quite rapidly after about 30 passes due to extinction of its mitotic potency such that it no longer allows viral expression.

In addition, the authors have envisaged a new approach (H. Perron et al., The Lancet, volume 337, 862–863, (1991)), which comprises taking a blood sample from a patient suffering from MS, culturing monocytes and collecting the supernatant to verify expression of a reverse transcriptase activity, either directly in the ultracentrifugation pellet or after equilibrium sedimentation over a sucrose gradient. It has thus been found that there is a reverse transcriptase activity peak in the supernatant of the patients suffering from MS, and that this activity is found in the fraction having a density of about 1.17 g/ml. Examination of the infected cells by electron microscopy has revealed particles similar to retroviruses of 100 to 120 nm which are found in the ultracentrifugation pellets of supernatants of cultures which express an increased reverse transcriptase activity. The centrifugation pellets containing cell debris and, potentially, viral particles were then cultivated on funicular blood cells to demonstrate a viral expression. However, as explained by the authors, a cytopathic effect was observed in the infected funicular blood cells, but is no longer detectable six weeks after inoculation, such that this culture method is not satisfactory for an in-depth study of the characteristics of this virus.

It was thus essential to have available a process for in vitro culture of cells infected by this virus.

SUMMARY OF THE INVENTION

A hypothesis has been put forward and verified, according to which permissive human plexus choroideus cells could be cells permissive to the virus found in patients suffering from MS. On the basis of this discovery, a process for in vitro culture of cells infected by a virus associated with MS has been developed.

The process comprises culture of plexus choroideus cells obtained after post mortem explantation of human plexus choroideus in a suitable medium comprising amino acids, vitamin factors, inorganic salts and glucose, in total weight concentrations respectively, of between 400 and 2250 mg/l, 3.5 and 130 mg/l, 9100 and 13,000 mg/l and 1000 and 6000 mg/l, to which a growth factor, such as ECGF ("Endothelial Cell Growth Factor"), to promote growth of the cells, and at least one antibiotic are advantageously added, then in bringing the plexus choroideus cells thus cultivated, in their culture medium, into contact with infected primary or derived cells or a supernatant of the culture comprising the virus under the given conditions allowing propagation of the virus from infected cells to cultivated cells, its replication and its expression.

Cells derived from primary cells are understood as meaning any culture obtained directly or indirectly from said primary cells, for example by storage at low temperature or maintenance of the viability of said cells. They may be, for example, reference cells deposited in a collection.

However, the propagation of the virus from a few infected cells, although this exists, remains relatively restricted in the course of successive passages and requires several passages to obtain a sufficient level of expression. Since the life of these cells in a culture is limited, it is often only at the last passages that expression becomes quantifiable, which considerably limits the usefulness of said procedure.

The works of the present inventors have led them to demonstrate, quite surprisingly, the production of beta-interferon by plexus choroideus cells in response to a viral attack. In fact, only fibroblasts, epithelial cells and macrophages are known to date for the production of interferon (Interferon: Principles and Medical Applications, the University of Texas Medical Branch at GALVESTON, Department of Microbiology, Galveston, Tex., 1992). The effects of interferons are well known, and in particular they induce a refractory state of cells to the synthesis and replication of viral material, thus inhibiting propagation and production of the viruses in the culture. It therefore became highly probable that the production of beta-interferon by plexus choroideus cells is a determining limiting factor in the process for in vitro culture of cells infected by a virus present in individuals suffering from multiple sclerosis.

On the basis of this unexpected discovery, the present inventors have developed a new culture medium which can be used in a process for in vitro culture of cells infected by a virus found in patients suffering from MS.

The present invention thus relates to a medium which is suitable for in vitro culture of cells infected by a virus present in individuals suffering from multiple sclerosis, which comprises, in addition to amino acids, vitamin factors, inorganic salts and glucose in total weight concentrations of, respectively, between 400 and 2250 mg/l, 3.5 and 130 mg/l, 9100 and 13,000 mg/l and 1000 and 6000 mg/l, and at least one anti-beta-interferon antibody.

More particularly, the medium comprises at least the following constituents:

one or more amino acids chosen from the following compounds:
arginine: 100 to 500 mg/l, preferably 100 to 300 mg/l
cysteine and/or cystine: 25 to 300 mg/l, preferably cystine: 25 to 100 mg/l
glutamine: 200 to 1000 mg/l, preferably 200 to 500 mg/l
histidine: 5 to 50 mg/l, preferably 5 to 20 mg/l
isoleucine: 20 to 100 mg/l, preferably 20 to 60 mg/l
leucine: 20 to 100 mg/l, preferably 20 to 60 mg/l
lysine: 20 to 100 mg/l, preferably 20 to 80 mg/l
methionine: 5 to 50 mg/l, preferably 5 to 30 mg/l
phenylalanine: 10 to 70 mg/l, preferably 10 to 50 mg/l
threonine: 15 to 100 mg/l, preferably 15 to 60 mg/l
tryptophan: 2 to 30 mg/l, preferably 2 to 25 mg/l
tyrosine: 10 to 70 mg/l, preferably 10 to 50 mg/l
valine: 10 to 60 mg/l, preferably 10 to 60 mg/l one or more vitamin factors chosen from the following compounds:
pantothenate: 0.15 to 5 mg/l, preferably the calcium salt: 0.15 to 2 mg/l
choline: 0.5 to 10 mg/l, preferably the chloride salt: 0.5 to 5 mg/l
folic acid: 0.5 to 10 mg/l, preferably 0.5 to 5 mg/l
inositol: 1 to 70 mg/l, preferably 1 to 50 mg/l
nicotinamide and/or niacinamide: 0.5 to 10 mg/l, preferably nicotinamide: 0.5 to 5 mg/l
pyridoxine and/or pyridoxal: 0.5 to 10 mg/l, preferably pyridoxine/HCl: 0.5 to 5 mg/l
riboflavin: 0.05 to 1 mg/l preferably 0.05 to 0.5 mg/l
thiamine: 0.5 to 10 mg/l, preferably 0.5 to 5 mg/l one or more inorganic salts chosen from the following compounds:
calcium salts: 100 to 200 mg/l, preferably anhydrous $CaCl_2$
potassium chloride: 350 to 450 mg/l
magnesium salts: 40 to 60 mg/l, preferably anhydrous $MgSO_4$
sodium chloride: 6000 to 8000 mg/l
$HCO_3$ salts: 2000 to 3000 mg/l, preferably $NaHCO_3$
$HPO_4$ salts: 600 to 1000 mg/l, preferably anhydrous $Na_2HPO_4$ glucose: 1000 to 6000 mg/l, preferably D-glucose
anti-beta-interferon antibodies: about 10 u/ml The amino acids are advantageously chosen from among those of the natural L series.

The medium can also comprise at least one antibiotic, preferably a mixture of penicillin and streptomycin, and, if desired, clindamycin to prevent mycoplasmic contaminations.

According to one embodiment of the invention, the medium furthermore comprises at least one growth factor chosen from ECGF ("Endothelial Cell Growth Factor", also called acid FGF) and basic FGF ("Fibroblast Growth Factor") in varying proportions as determined by the expert from his general knowledge of cell cultures and products available to him. By way of example, the concentration of growth factor is between 1 and 50 µg/l of culture medium, in the presence of heparin at a concentration of between 50 and 50 µg/l. The growth factor chosen is advantageously ECGF (10 µg/l, in the presence of heparin as above).

The invention also relates to a process for in vitro production of a culture of infected human plexus choroideus cells, sampled post mortem from the body of an individual or patient suffering from MS, according to which said cells sampled are cultivated in the above-mentioned culture medium and under the given conditions to obtain a first culture of primary plexus choroideus cells, and a sample of said culture of primary cells or of a subculture of the latter is then cultivated in series, that is to say by successive passages, in said culture medium to obtain a culture of infected plexus choroideus cells.

The invention also relates to an infected cell line of plexus choroideus cells obtained in accordance with the process described above, called PLI-2, in accordance with the provisions of the Treaty of Budapest, and deposited at the ECACC on Jul. 22, 1992 under number 92072201, and to the viral strain which it harbors, called POL-2 and deposited at the ECACC the same day under nether V92072202. These two depositions were made under the authority of and in accordance with the provisions of the Treaty of Budapest.

The cells of the line PLI-2 are advantageously transfected by an "immediately precocious" gene of a virus of the genus Herpesviridae to increase the viral expression in these cells.

The invention also relates to a process for the production of a viable or continuous infected cell culture or line comprising cells infected by at least one human viral strain associated with MS, which comprises:

(a) cultivation of human cells infected by the viral strain to obtain at least one primary or derived culture infected by said strain, (b) cultivation of permissive human cells, preferably of non-infected human plexus choroideus cells obtained in accordance with the process described above, said permissive cells being capable of becoming infected with and of replicating said viral strain, to obtain at least one permissive culture, (c) cocultivation of at least one sample of a primary infected culture and one sample of a permissive culture, to obtain a primary derived culture infected by a said viral strain, (d) cultivation in series, that is to say by successive subcultures, of the first derived infected culture; for this purpose, the stage comprising cocultivation, for example over 5 to 8 days, of a new sample of a non-infected permissive culture and a sample of the first derived infected culture, or of a subculture of the latter, is repeated in the course of time, to obtain a new subculture of the same first derived infected culture constituting a continuous viral culture in non-immortal cells.

Culture derived from the primary culture is understood as meaning any culture or subculture obtained directly or indirectly from said primary culture by storage at low temperature or, for example, by maintaining the viability of said culture. It may be, for example, a reference culture deposited in a collection.

At least any one of stages (a) to (d) is carried out with a culture medium comprising an anti-beta-interferon antibody.

The primary infected culture is advantageously obtained from human cells infected by said viral strain resulting from the in vitro production process described above, for example the cell line 92072201 of the ECACC, and/or from human cells infected by said viral strain chosen from the group comprising leptomeningeal cells, plexus choroideus cells, myeloid blood cells, in particular macrophages and monocytes, and lymphocytes.

The permissive culture is preferably obtained from human plexus choroideus cells.

Finally, the invention relates to a viable or continuous viral culture obtained according to the above process.

The cells harboring said continuous viral strain are advantageously transfected by at least one "immediately precocious" gene of a virus of the genus Herpesviridae to increase viral expression in these cells.

The use of human anti-beta-interferon sera or antibodies has allowed increased propagation of viral strains present in cells explanted from anatomical specimens or introduced into non-infected plexus choroideus cells by coculture. It has thus been possible to increase global expression of the virus in plexus choroideus cell cultures and to shorten the time before a detectable signal is obtained after culture of pathological isolates. These effects can be attributed to the neutralization by the beta-interferon antibodies or an antigenically close molecule which plays an inhibiting role in viral expression and is produced by these cells in the presence of the virus.

"Anti-beta-interferon antibody" is understood as meaning any preparation comprising antibodies of mono- or polyclonal origin which may or may not be purified (for example by affinity chromatography) and which recognize epitopes belonging to human beta-interferon or to any analogous antigenic molecule which plays an inhibiting role in viral expression.

According to a particular embodiment of the invention, the primary infected culture is first treated by irradiation, for example by irradiation with X-rays, before being brought into contact with the permissive cultivated cells.

According to a particular embodiment of the invention, several primary cultures infected by viral strains or MS isolates which differ respectively are obtained, and during stage (b), samples of said primary cultures or subcultures of the latter, which differ respectively, are cocultivated. The cell culture of a mixture of viral strains are thus obtained, allowing inter-strain recombination, possible complementation of defective genomes and the emergence of recombinant strains, the suitability of which for certain criteria can be greatly increased. This may allow, in particular, production of a strain highly suitable for in vitro culture or production of replicative strains from defective strains.

The invention also relates to a process for the detection of antibodies directed against a virus associated with MS in a biological fluid.

The invention also relates to a process for the production of a vaccine preparation from infected cells obtained according to the process of the invention or the virus produced by said cells.

The term "infected cells" as used in the present invention refers:

i) to primary infected cells obtained from a culture of cells resulting directly from in vivo or post mortem sampling of biological tissues or fluids from an individual, and to derived cells obtained by passages of these primary cells, and ii) to secondary infected cells obtained by coculture of primary infected cells and of permissive cells, and to derived cells obtained by passages of these secondary cells.

"Primary cells" is understood as meaning culture cells originating directly from sampling biological tissues or fluids and passed in culture without any coculture or inoculation by viral strains resulting from other cells.

The cells removed in vivo or post mortem can be any cells infected by the virus, for example leptomeningeal cells isolated from the cephalorrachidian fluid of a patient (H. Perron et al., Res. Virol., 140, 551–561 (1989)), myeloid cells found in the blood, in the cephalorrachidian fluid, in tissues or in bone marrow, in particular macrophages or monocytes (H. Perron et al., The Lancet, volume 337, 862–863, Apr. 6, 1991) and also lymphocytes (S. Haahr et al., The Lancet, volume 337, 863–864, Apr. 6, 1991) or analogous cells. Another candidate for preparation of a culture of primary cells is represented by human plexus choroideus cells, which are presumed to be a dormancy site for a virus associated with multiple sclerosis.

The term "macrophage(s)" refers to cells derived directly from blood monocytes, to cells residing in tissues (for example microgliocytes or Kupfer cells) and cells of the reticulo-endothelial system, in particular Langerhans cells.

Permissive cells are cells which can become infected with and allow replication of a given virus with production of viral particles, in particular extracellular particles, which can be studied, for example in respect of their reverse transcriptase activity in supernatants.

The term "passage" refers to a cell culture and corresponds to dissociation of cells from a culture flask for transfer into one or more new flasks.

It is well-known to experts that spontaneous or induced modifications can survive in the karyotype during storage or passages. Cells derived from a reference cell line thus cannot be exactly identical to cultures or starting cells. Furthermore, the genetic variability of retroviruses is well known, and a given retroviral strain may modify its characteristics by spontaneous or induced mutations in the course of cultures.

The invention generally relates to any biological cell material which can be used directly or indirectly for various purposes, for example therapeutic, clinical, diagnostic or analytical purposes, comprising:

either cells sampled from or belonging to a cell culture or line infected by a human viral strain associated with MS and obtained by any of the processes described above, for example the cell line called PLI-2, deposited at the ECACC on Jul. 22, 1992 under number 92072201 in accordance with the provisions of the Treaty of Budapest or derived cells obtained by modifying the genome of said cells spontaneously or artificially, but without alteration of their phenotype of cells infected by a virus associated with MS.

The virus present in the biological cell material can preferably be transactivated according to the process for transfection described above such that the virus associated with MS is expressed more intensively, more quickly and/or more completely.

The invention also relates to any viral biological material which can be used directly or indirectly for various purposes, in particular for clinical, therapeutic, diagnostic or analytical purposes, this material comprising:

either a viral fraction obtained from the biological cell material defined above, if appropriate after transactivation of the viral element, for example obtained by separation of viral particles from the supernatant of infected cells or by antigen fractionation; this viral fraction results, for example, from the viral strain called POL-2, deposited at the ECACC on Jul. 22, 1992 under number V 92072202 in accordance with the provisions of the Treaty of Budapest or a viral fraction derived from said viral particles, obtained by modifying the genome and/or the envelope and/or the nucleocapsid of viral particles of said fraction spontaneously or artificially.

The invention also relates to a process for detection of the presence of antibodies directed against an MS virus in any biological fluid samples from the human body. For this purpose, it is sufficient to bring a sample of this biological fluid into contact with either an antigenic extract of the biological cell material defined above or an antigenic extract of a viral biological material as defined above, or all or some of an antigenic extract immunologically analogous to said virus which is obtained by chemical synthesis or genetic recombination and comprising at least one epitope of a viral strain associated with MS; the presence of an antibody/epitope complex is then investigated by any suitable means, for example by a chromogenic, chromophoric or radioactive reaction.

The invention also relates to any immunological reagent, in particular monoclonal or polyclonal antibodies, which have an immunological reaction with a naturally occurring or synthetic antigenic extract as defined above.

Finally, the invention also relates to any vaccine preparation comprising:

either an antigenic extract from a biological cell material or from a viral biological material as defined above which is dead or inactive or attenuated, or an immunoreactive compound which induces an immunological reaction analogous to that caused against said antigenic extract.

The invention will be better understood by reading the detailed description which is to follow, with reference to the figures attached, in which.

Figure 2:
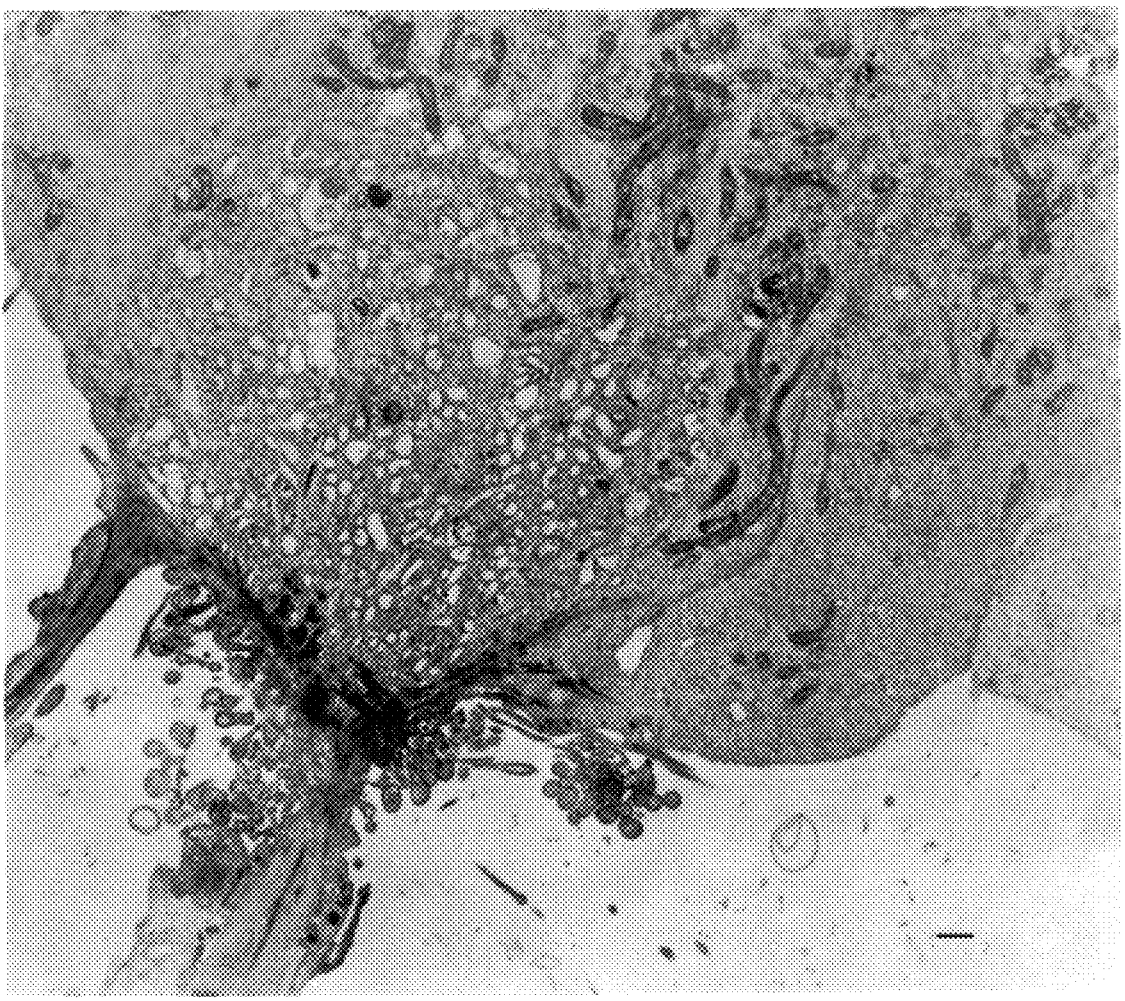
FIGS. 2 to 5 represent particles of the retroviral type observed in the PLI-2 cells by electron microscopy after transactivation by transfection of plasmids containing the ICP0 or ICP4 gene of the herpes simplex type 1 virus. The scales are in $\mu$m.
Figure 3:
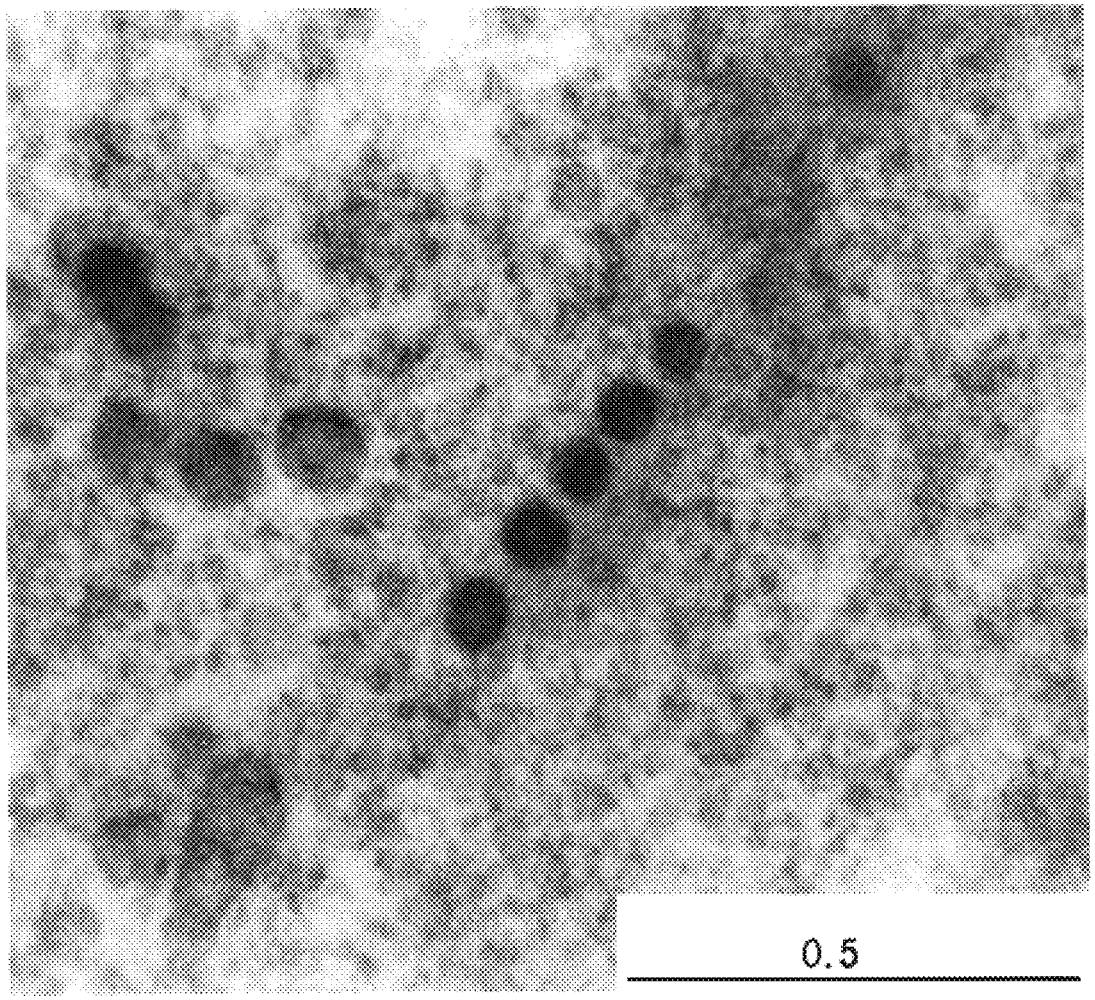
Figure 4:
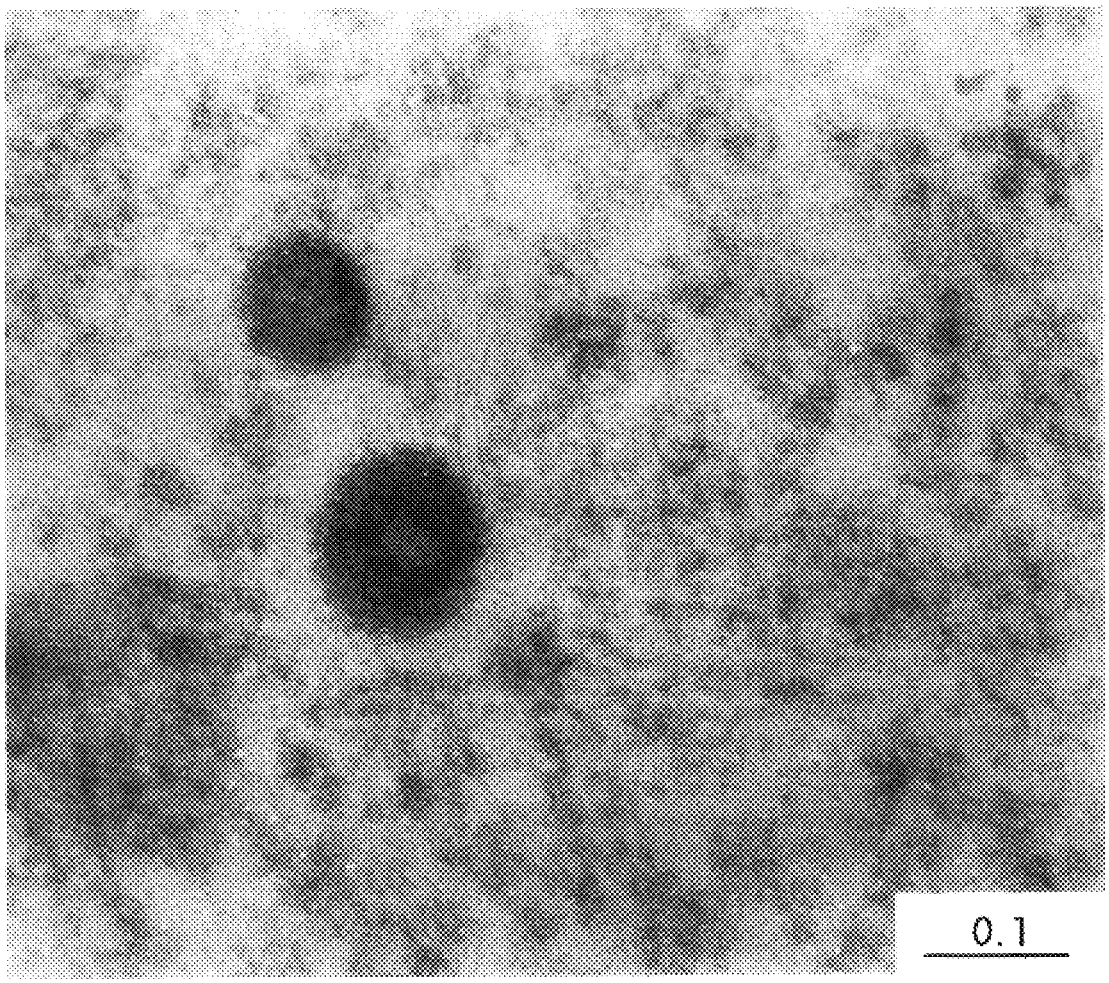
Figure 5:
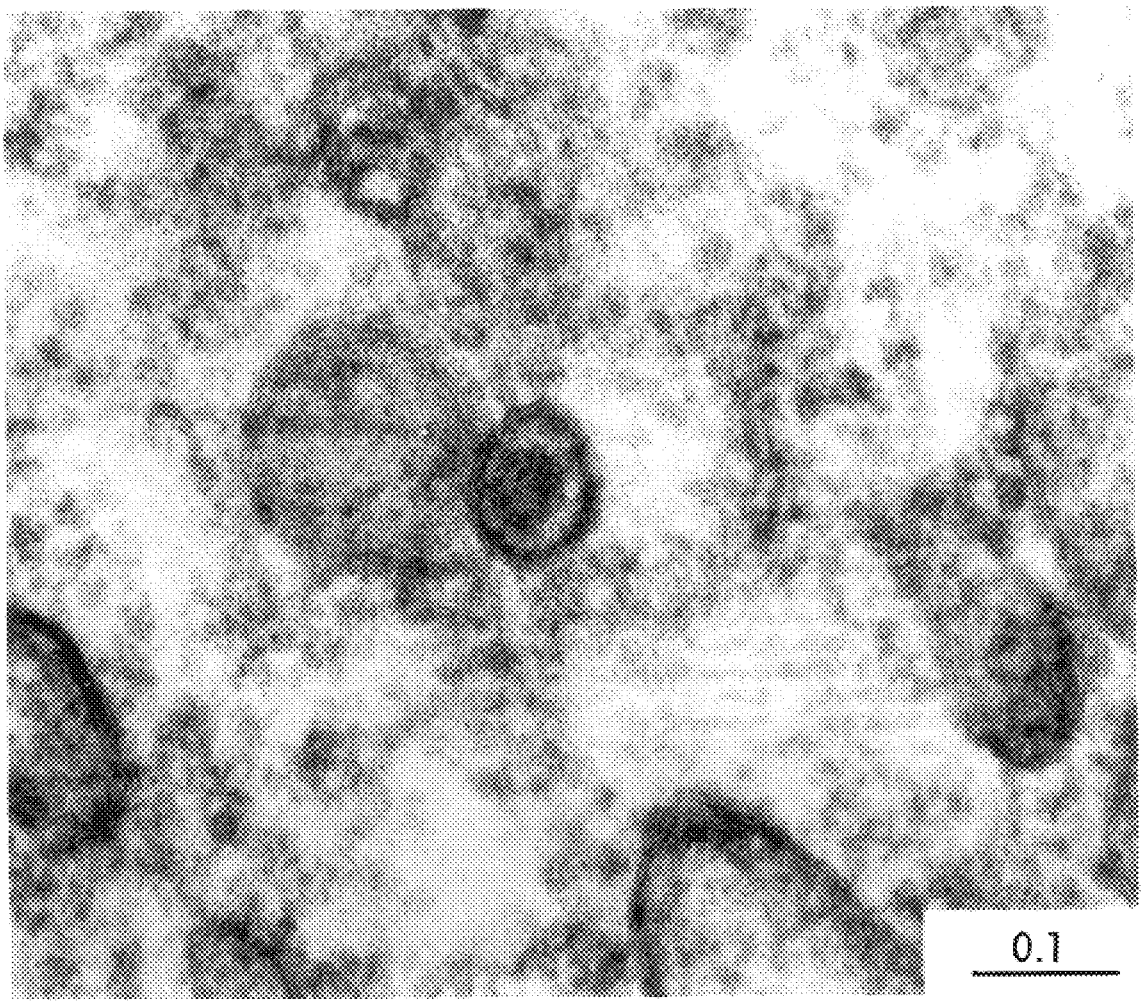

More particularly, FIG. 2 represents a part of the PLI-2 cell (the scale shown corresponds to 1 $\mu$m). FIG. 3 represents particles of the retroviral type corresponding to intracytoplasmic nucleocapsids as observed in an increased number after stimulation (transactivation) by the product of the ICP0 gene of the herpes simplex Type 1 virus. FIG. 4 represents a more highly magnified detail of intracytoplasmic particles. FIG. 5 represents a detail of a particle of more mature appearance in PLI-2 cells stimulated by transfection with the gene ICP4 of the herpes simplex Type 1 virus.

EXAMPLE 1

Demonstration of the Production of Beta-interferon by Plexus Choroideus Cells

Plexus choroideus cells in culture in vitro and infected by the strain LM7 described above were dissociated by a solution of trypsin or EDTA, transferred into a tube containing, as appropriate, a small amount of fetal calf serum in the case of trypsin dissociation of cells resistant to the action of EDTA by itself, and were sedimented by centrifugation at 1600 revolutions per minutes for 5 to 15 minutes. The cell pellet was resuspended in PBS ("Phosphate-Buffered Saline") buffer and one drop of suspension was deposited in each eye of a few slides for microscopy. After the deposit had been dried, the slides were fixed by incubation in a mixture of methanol and acetone (1 volume/1 volume) at −20° C. for 15 minutes.

Alternatively, these same cells were cultivated on slides with culture cups (marketed by the company Labtek) and, after rapid rinsing in PBS, were fixed as above.

Several dilutions, in PBS, of human anti-beta-interferon monoclonal antibody (Boehringer Mannheim, ref. 853 577;

dilutions: 1/250, 1/500, 1/1000, 1/2000) or polyclonal antibody (VIE 3000-ZI LA TUFFARDE 01360 BALAN FRANCE; dilutions: 1/50, 1/100, 1/500, 1/1000) were deposited on slides and incubated for 3 hours at 37° C. The slides were then rinsed for a few minutes in two successive baths of PBS and then in a bath of distilled water. After the slides had been dried, appropriate dilutions of mouse anti-IgG, for the monoclonal antibody, and goat anti-IgG, for the polyclonal antibody, antibodies labeled with the fluorochrome were deposited respectively on the corresponding slides, which were then incubated for 1 hour at 37° C. The slides were then rinsed as above and, after drying, mounted for observation under a fluorescence microscope.

For better visualization of the surrounding cell structures, some slides were incubated for about 1 minute in a solution of "Evans Blue" stain and then rinsed and dried before being mounted.

The presence of a specific immunological reaction revealed by emission of a fluorescence was thus demonstrated, which confirms production of anti-beta-interferon by plexus choroideus cells.

For confirmation, plexus choroideus cells were infected by a highly replicative virus in accordance with the following protocol.

Non-infected plexus choroideus cells were cultured in flasks of the "Labtek" type in the medium described in Example 3 below, but in the absence of anti-beta-interferon antibody.

These cells were then infected by the herpes simplex virus type 1 (HSV-1). After contact with a supernatant containing ESV-1 virions for about 1 hour, they were then left overnight.

The following day, the supernatants were removed and frozen at −80° C., and the slides constituting the flasks on which the cells grew were removed from the cups and, fixed in paraformaldehyde and then used, as were slides of non-infected cells, for analysis by a conventional immunoperoxidase technique with anti-beta-interferon polyclonal antibodies (example: human anti-beta-interferon goat polyclonal antibodies marketed by VIE-3000, France) and development by a secondary antibody labeled with peroxidase (example: goat anti-immunoglobulin rabbit antibody).

Specific labeling of the plexus choroideus cells infected by a highly replicative virus such as HSV-1 by the anti-beta-interferon antibodies was thus demonstrated; this is not the case with non-infected cells.

This confirms the production of beta-interferon by plexus choroideus cells in response to viral aggression.

EXAMPLE 2

In vitro Preparation of a Culture of Primary Cells Infected by a Virus Present in a Patient Suffering from MS The methods for preparation of primary cell cultures starting from infected cells, for example from leptomeningeal cells, monocytes or lymphocytes, and the conditions for their growth in vitro are known to the expert (see the references above).

EXAMPLE 3

Preparation of a Culture of Infected Human Plexus Choroideus Cells

Infected plexus choroideus cells are obtained after post mortem explantation of human plexus choroideus from a patient. The anatomical specimen removed under sterile conditions is delicately delacerated with tweezers and placed in a trypsin solution at about 37° C. for few minutes. The tissue fragments are collected after centrifugation at a low speed (500 revolutions/minute) and the supernatant is centrifuged at 16,000 revolutions/minute for 5 to 15 minutes. The centrifugation pellet is taken up in RPMI 1640 medium (marketed by Boehringer Mannheim) comprising: penicillin (200,000 U/l), streptomycin (200 mg/l), clindamycin (75 mg/l), L-glutamine (6 mM/l), 1% of pyruvate, serum, preferably 20 to 30% of fetal calf serum decomplemented by incubation at 56° C. for 30 minutes, 1% of non-essential amino acids (Boehringer Mannheim HEM, A.A.N.E. 100X ref: 210293) and human anti-beta-interferon antibodies in the polyclonal form as marketed by VIE 3000 or in the monoclonal form having a neutralizing activity with respect to beta-interferon (10 U/ml). The culture medium moreover advantageously comprises a growth factor, such as endothelial cell growth factor (ECGF), combined with heparin (BOEHRINGER ref. 1/79/87: ECGF about 1 to 20 ng/ml, comprising 50–150 µg/ml of heparin).

The cells are kept in their culture medium and then placed in an incubating cabinet under $CO_2$ until cell proliferation produces a confluent layer, that is to say a carpet of adhering cells. At this stage, the cells are dissociated with an EDTA solution (Versène). The cell cultures are then regularly divided in two for as long as the mitotic potential allows. The culture media are changed at least twice a week, and always on the day following a new passage, that is to say at each new seeding of a flask with suspended dissociated cells.

A progressive extension of the mitotic potency of infected cells is observed after about 15 passages, which agrees with observations made in the absence of anti-beta-interferon antibodies. However, as is never found in the process for culture of infected plexus choroideus cells in vitro in a culture medium deprived of anti-beta-interferon antibodies, some clonal proliferation foci appeared progressively after the last passage of infected plexus choroideus cells sampled from a patient suffering from MS. It was possible to subculture three of these foci, and one of them became established in a line of high growth potential in vitro. This line has been called PLI-2 by the Applicant.

The supernatants from the culture of this established line of infected plexus choroideus cells of a minimum volume of 15 ml were collected, precentrifuged at 10,000 revolutions per minute for 30 minutes, to remove the cell debris, and then ultracentrifuged at 35,000 revolutions per minute (100,000 g) for 2 hours for sedimentation of the retroviral particles. The pellets were collected (final volume concentrated about 1000 times in buffer, 0.05 M Tris HCl, pH 9.5) and kept at −80° C. for subsequent analysis of the reverse transcriptase activity and preparation of the concentrated virus as described below.

EXAMPLE 4

Analysis of the Reverse Transcriptase Activity for Monitoring the Production of Viral Particles of the LM7 Type in the Supernatant of PLI-2 cells All the steps were carried out with sterile material and solutions in order to avoid any interference from bacterial nucleases or proteases, in particular during the incubation phases at 37° C.

The pellets containing the viral particles concentrated in 0.01 M Tris HCl, pH 8 are thawed and homogenized. 20 µl are taken and added to a reaction mixture comprising: 5 µl of (0.5 M Tris+0.04 M DTT) pH 8.2, 5 µl of 0.1 M NaCl, 5 µl of 0.3 MgCl$_2$, 23 µl of doubly distilled H$_2$O, 10 µl of 2% strength NP$_4$O, 2 µl of polyCm-oligodG12-18 (10 ODU/ml; Pharmacia) and 5 µl of 3E,3H-guanosinetriphosphate (1 mCi/ml; NEN). The glass tubes containing the mixtures are incubated at 37° C. for 75 minutes. The reaction is stopped by adding 75 µl of a solution, at +4° C., comprising: 12.5% of H$_2$O saturated with sodium phosphate, 12.5% of H$_2$O saturated with sodium pyrophosphate and 20% of trichloroacetic acid (TCA). After 30 minutes to 1 hour at 4° C., the tubes are filled with a 5% strength solution of TCA, emptied and rinsed 5 times with the 5% strength solution of TCA over a cellulose acetate membrane (Sartorius ref. 11106 25 N; pore diameter: 0.45µ; membrane diameter: 25 mm), through which the samples are filtered into a 1125 fraction collector (Millipore, ref. XX2702550). Before being removed, the membranes are rinsed once more with 20 ml of 5% strength TCA. The membranes are then placed in small flasks which are filled with scintillating liquid (Ready-Safe, Beckman) and the activity is measured in a beta-counter in cpm (counts per minute) and dpm (disintegrations per minute).

Each sample is tested in triplicate and the mean of the values is used as the result. If the difference between this mean and one of the measurements exceeds twice the standard deviation measured over the reference values, the corresponding sample is tested again.

Figure 1:
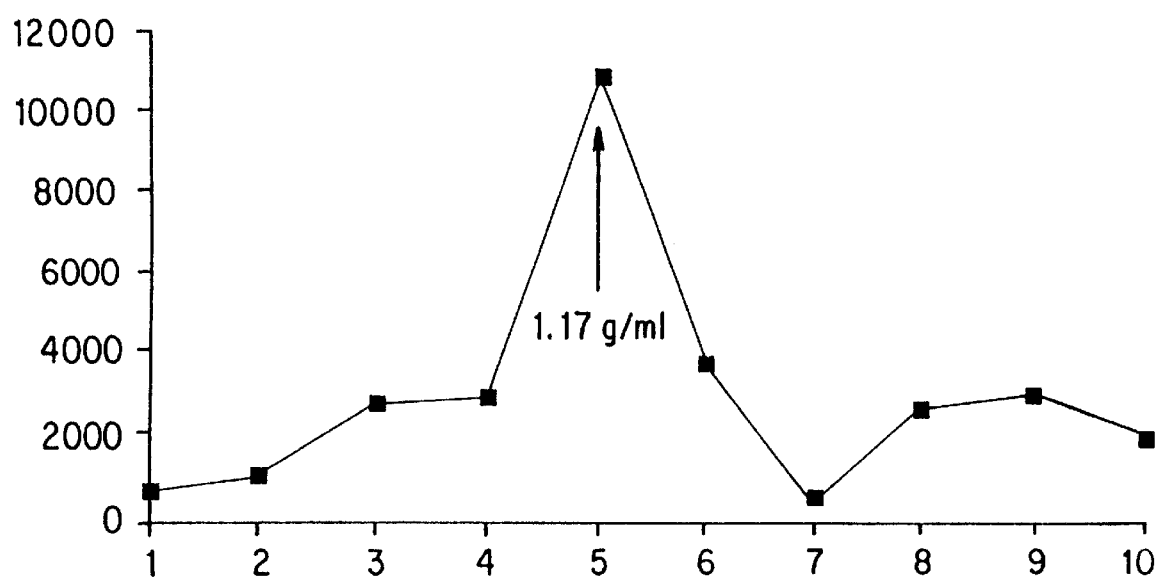
FIG. 1 represents the reverse transcriptase activity of particles concentrated from culture media of the line PLI-2 which sediment over a gradient of sucrose at a density known for retroviruses.

To check that the reverse transcriptase activity is definitely associated with particles of the retroviral type, the virion pellets concentrated by ultracentrifugation of the supernatants of the culture on a cushion of glycerol (PBS solution +30% of glycerol) are placed over sucrose gradients (15 to 50% weight/weight) and ultracentrifuged at +4° C. for 6 to 16 hours at 35,000 revolutions per minute (100,000 g) in a cup rotor. 10 fractions are collected and 20 µl are taken from each fraction to analyze their reverse transcriptase activity as described above. The specific activity peak is found in the fraction having a density of about 1.17 g/ml (refractometric analysis), which corresponds to an equilibrium sedimentation density known for retroviral particles (1.16 to 1.18 g/ml) (FIG. 1).

EXAMPLE 5

Transfection of Cells of the PLI-2 Line by "immediately precocious" Genes of the Herpes Simplex Virus Type 1

As has been shown (Perron et al. Res. Virol. 1989), the herpes simplex type 1 virus (HSV-1) stimulates production of the LM7 virus in leptomeningeal cells. Furthermore, HSV-1 has been proved to transactivate expression of the HIV retrovirus by the product of one of its "immediately precocious" genes, ICP0 or IE1 (Chapman J. C., Harris J. D., Collins M. K. L. & Latchman, D. S. 1991, A recombinant HIV provirus is synergistically activated by the HIV Tat protein and the HSV IE1 protein but not by the HSV IE3 protein. AIDS 5, 945–950 and Mosca, J. D. Bednarik, D. P. Raj, N. B. Rosen, C. A. Sodroski, J. G. Haseltine, W. A. & Pitha, P. M. 1987. Activation of human immunodeficiency virus by herpes virus infection: identification of a region within the long terminal repeat that responds to a trans-acting factor encoded by herpes simplex virus 1. Proceedings of the National Academy of Sciences 84, 7408–7412).

On the basis of these findings, the inventors thus envisaged the use of "immediately precocious" genes of the HSV-1 virus to increase viral expression by the PLI-2 cell line. Various plasmids each containing an immediately precocious gene of the HSV-1 virus were therefore tested by transfection into infected plexus choroideus cells. It was thus demonstrated, by electron microscopy and analysis of the reverse transcriptase activity, that the ICP0 genes (cloned in the plasmid pJR3) and ICP4 genes (cloned in the plasmid XhoC) greatly transactivated expression of a virus similar to LM7 in cells of the PLI-2 line (FIGS. 2 to 5). Viral particles of about 100 nm are found in the ultracentrifugation pellets of supernatants of these cultures expressing an increased reverse transcriptase activity.

The experimental protocol of the transfection is described below.

The plasmid pJR3 contains a Pst I-SacI restriction fragment of HSV-1 (nucleotides 18663 to 25066) which encode ICP0, cloned in a pUC9 vector. Plasmid XhoC is a XhoI restriction fragment of HSV-1 (nucleotides 23028 to 33520) which encode ICP4, cloned in a pAT153 vector.

The transfection is carried out with Transfectam (registered trade mark, SEPRACOR, Villeneuve la Garenne, France). The principle of this transfection comprises a specific interaction between a cationic lipopolyamine and the plasmid DNA.

The plasmids are diluted in a sterile 0.3 M solution of NaCl in an amount of 2 µg/250 µl and 5 to 7 µg/10$^6$ cells. Immediately before the transfection, this solution is mixed with the same volume of doubly distilled water containing 5 µl of Transfectam stock solution per µg of plasmid. This Transfectam-plasmid mixture is then poured onto the cultures, previously washed with RPMI without serum (2×15 minutes), and the components are mixed with a minimum volume of medium according to the invention, but without foetal calf serum, which is introduced into the flasks such that the surface of the monolayer of adhering cells is covered. The culture flasks are then incubated for 6 hours in an incubating cabinet with 5% of CO$_2$ at 37° C. After 6 hours, the Transfectam/plasmid mixture is removed and replaced by culture medium according to the invention.

The cells are reincubated in the incubating cabinet and the supernatants are sampled about one day after the 6 hours of contact with the transfection mixture, and then every day for one week. The supernatants, including that which contains the Transfectam with the plasmid, are kept at −80° C., or concentrated as described in Example 6 below, and subsequently used as an enriched source of virions.

Expression of the ICP0 or ICP4 genes in the transfected cells is verified by indirect immunofluorescence with rabbit polyclonal or mouse monoclonal antibodies against the proteins produced by these genes.

EXAMPLE 6

Preparation of Concentrated Purified Virus from Culture Supernatants of the PLI-2 line For preparation of concentrated and purified virus, a volume of supernatant obtained according to Example 3 or 5 (between 5 and 10 liters) is thawed and concentrated by tangential ultrafiltration (Minitan system, Millipore) over a series of membranes having a separation threshold of 300,000 daltons. The concentrate is then centrifuged in accordance with Example 3, but with the pellet being taken up in PBS buffer. The pellets thus collected are then combined and deposited on a gradient of sucrose in a sterile PBS buffer (15 to 50% weight/weight), and subjected to ultracentrifugation at 35,000 revolutions per minute (100,000 g) for 6 hours at +4° C. in a cup rotor. 10 fractions are collected and 20 µl are sampled from each fraction for analysis of their reverse transcriptase activity in accordance with the technique described above. The fractions containing the specific activity peak corresponding to an equilibrium sedimentation density of between 1.16 and 1.18 g/l, which is known for retroviral particles, are then diluted in sterile PBS buffer and ultracentrifuged for one hour at 35,000 revolutions per minute (100,000 g) for sedimentation of the viral particles. The pellet of purified virions thus obtained is then taken up in a small volume of buffer sufficient for its subsequent intended use (example: guanidine thiocyanate buffer for extraction of the RNA; sterile PBS for storage at −60° C.).

Alternatively, large amounts of flasks of PLI-2 cells can be cultured and the supernatants, the total volume of which exceeds 2 liters at each change of medium, are precentrifuged at 10,000 revolutions per minute and then concentrated directly with the Minitan system (registered trade mark, Millipore) without intermediate freezing.

EXAMPLE 7

Coculture of a Cell Line Infected by a Virus present in an Individual Suffering from MS and of Non-infected Cells Permissive to the Virus Cells of a primary culture infected, as described in Example 2, by a virus present in an individual suffering from MS, for example the LM7 virus, are sampled from their culture flask and then taken up in a culture medium suitable for coculture, that is to say the culture medium of the infected plexus choroideus cells described in Example 3, with a human anti-beta-interferon antibody.

In parallel, non-infected plexus choroideus cells obtained after post mortem explanation of the human plexus choroideus are cultivated under the conditions of Example 3, that is to say with a human anti-beta-interferon antibody. These cells are then dissociated from their culture flask in a solution of trypsin/EDTA. The cells are then centrifuged and resuspended in their culture medium, and are added to the flask of the infected cell culture. The flask is placed in an incubating cabinet under $CO_2$ and the plexus choroideus cells are allowed to adhere and proliferate at the bottom of the flask already containing infected cells for 24 hours. The medium is changed after 24 hours and the mixture of cells is left in the incubating cabinet under $CO_2$ until proliferation of permissive plexus choroideus cells produces a confluent layer, that is to say a carpet of adhering cells. At this stage, the cells are kept for a further 5 to 7 days to ensure transfer of the virus from the infected cells to the plexus choroideus cells. The cell culture is then divided in two and placed in two new flasks, which are reseeded with the suspended dissociated plexus choroideus cells, and subjected to the same conditions as described above for adhesion and proliferation of the cells, transfer, and expression and replication of the virus. The cell cultures and then divided in two regularly and subjected to passage for as long as the mitotic potential of the permissive cells allows. These cells, which harbor and produce a virus of the LM7 type, can in turn be used to infect new cells by coculture as described above, and thus to maintain the viral strain in culture.

The culture media are always changed at least twice a week, and always the day following a new passage, that is to say at each new seeding of a flask with suspended dissociated cells.

Prior to coculture, the cells which harbor the viral strain can be irradiated, if appropriate, in order to prevent their subsequent proliferation within a newly infected culture. The irradiation can be carried out, for example, with a total doze of 6000 rad of X-rays.

An extinction in the mitotic potency in observed after about 15 passages, which is in agreement with the findings made above in the absence of anti-beta-interferon antibodies.

However, as demonstrated with the culture of infected plexus choroideus cells of Example 3, a few clonal proliferation foci appeared in several flasks in culture after the last passage. This same phenomenon led to the appearance of cells of high mitotic potential, which displaced the presenescent cells in a subculture of the strain LM7 (called LM7 PG).

The culture supernatants of this established line were collected and frozen at −80° C. in accordance with the protocol described in Example 3.

Analysis of the reverse transcriptase activity for monitoring of the viral particles of type LM7 in the supernatant of LM7 PG cells was carried out in accordance with the experimental protocol described in Example 4, and allowed the demonstration of a specific activity peak in the fraction having a density of about 1.17 g/ml, which corresponds to a density known for retroviral particles (FIG. 1).

The cells of the LM7 PG cell line were then transfected in accordance with a protocol identical to that described in Example 5, which showed that the ICPD genes (plasmid pJR3) and ICP4 genes (plasmid XhoC) greatly transactivate viral expression in the cells of the LM7 PG line. The viral particles produced show the characteristics of retroviruses.

The purified concentrated virus is prepared from the supernatants obtained either directly after coculture or by transfection of cells of the LM7 PG line with the ICP0 and/or ICP4 genes of the ESV-1 virus.

We claim:

1. A process for in vitro production of a culture or cell line infected by a viral strain, said viral strain having at least one of its replication and expression inhibited by a molecule which plays an inhibiting role in viral expression, said process comprising:

obtaining a body sample from an individual infected with said viral strain, cultivating said body sample in a culture medium which promotes growth of infected cells to obtain a culture or cell line of primary infected cells, and cultivating by successive passages in said culture medium a sample of the culture or cell line of primary infected cells or a subculture of said culture or cell line to obtain the culture or cell line infected by said viral strain, wherein the culture medium also contains an antibody directed against said molecule which plays an inhibiting role in viral expression, and said culture medium allows persistent expression and propagation of the viral strain in the culture or cell line.

2. A culture medium for carrying out a process as claimed in claim 1, comprising at least one amino acid, at least one vitamin factor, at least one inorganic salt, glucose, and said antibody directed against said molecule which plays an inhibiting role in viral expression.

3. The culture medium according to claim 2, further comprising said viral strain.

4. The process according to claim 1, wherein said molecule which plays an inhibiting role in viral expression is beta-interferon or a molecule antigenically close to beta-interferon.

5. The process according to claim 4, wherein said viral strain is associated with multiple sclerosis.

6. The process according to claim 1, wherein said viral strain is associated with multiple sclerosis.

7. The culture medium according to claim 2, wherein said molecule which plays an inhibiting role in viral expression is beta-interferon or a molecule antigenically close to beta-interferon.

8. The culture medium according to claim 3, wherein said molecule which plays an inhibiting role in viral expression is beta-interferon or a molecule antigenically close to beta-interferon.

9. The culture medium according to claim 3, wherein said viral strain is associated with multiple sclerosis.

10. The culture medium according to claim 8, wherein said viral strain is associated with multiple sclerosis.

11. The process according to claim 4, wherein said molecule which plays an inhibiting role in viral expression is beta-interferon.

12. The culture medium according to claim 7, wherein said molecule which plays an inhibiting role in viral expression is beta-interferon.

13. The culture medium according to claim 8, wherein said molecule which plays an inhibiting role in viral expression is beta-interferon.

* * * * *

UNITED STATES PATENT AND TRADEMARK OFFICE
CERTIFICATE OF CORRECTION

PATENT NO. : 6,071,736
DATED : June 6, 2000
INVENTOR(S) : Herve Perron and Jean-Marie Seigneurin It is certified that error appears in the above-identified patent and that said Letters Patent is hereby corrected as shown below:

<u>Title page,</u>
Item [30], please change "Apr. 3, 1993" to -- Apr. 3, 1992 --.

Signed and Sealed this

Eighth Day of October, 2002

*Attest:*

*Attesting Officer*

JAMES E. ROGAN
*Director of the United States Patent and Trademark Office*